US010887722B2

(12) United States Patent
Borrel

(10) Patent No.: US 10,887,722 B2
(45) Date of Patent: Jan. 5, 2021

(54) TRAFFIC POLLUTION MAPPER

(71) Applicant: Herve Borrel, Scottsdale, AZ (US)

(72) Inventor: Herve Borrel, Scottsdale, AZ (US)

(73) Assignee: Airlib Inc., Scottsdale, AZ (US)

( * ) Notice: Subject to any disclaimer, the term of this patent is extended or adjusted under 35 U.S.C. 154(b) by 225 days.

(21) Appl. No.: 15/154,732

(22) Filed: May 13, 2016

(65) Prior Publication Data

US 2017/0272338 A1 Sep. 21, 2017

Related U.S. Application Data

(60) Provisional application No. 62/308,966, filed on Mar. 16, 2016.

(51) Int. Cl.
| | | |
|---|---|---|
| *H04W 4/02* | (2018.01) | |
| *H04W 4/029* | (2018.01) | |
| *H04W 4/024* | (2018.01) | |
| *H04L 29/08* | (2006.01) | |

(Continued)

(52) U.S. Cl.
CPC ........ *H04W 4/023* (2013.01); *G01N 33/0036* (2013.01); *G01N 33/0063* (2013.01); *H04L 67/12* (2013.01); *H04L 67/18* (2013.01); *H04W 4/024* (2018.02); *H04W 4/029* (2018.02); *H04W 4/44* (2018.02)

(58) Field of Classification Search
None
See application file for complete search history.

(56) References Cited

U.S. PATENT DOCUMENTS

| 4,320,797 A * | 3/1982 | Kagohata ........... B60H 1/00642 |
| | | 165/204 |
| 4,875,406 A | 10/1989 | Hotler et al. |
| 5,217,692 A | 6/1993 | Rump et al. |

(Continued)

FOREIGN PATENT DOCUMENTS

| CN | 20121590228 | 7/2014 |
| CN | 20142402720 | 1/2015 |

(Continued)

OTHER PUBLICATIONS

Srinivas et al. "Real-time Air Quality Monitoring Through Mobile Sensing in Metropolitan Areas", Aug. 11, 2013, ACM.*

(Continued)

*Primary Examiner* — Aaron N Strange
*Assistant Examiner* — Mohammad Yousuf A. Mian
(74) *Attorney, Agent, or Firm* — Lightbulb IP, LLC

(57) ABSTRACT

A traffic pollution mapper detects pollution variations and generates mapping information for establishing one or more pollution maps. The traffic pollution mapper includes one or more pollution detectors, installed on vehicles, that detect pollution and generate pollution information from the same as the vehicles travel through traffic. This pollution information may be combined with location information and a timestamp to create mapping information that is stored on a server. The mapping information may be queried by one or more client devices in various formats, including as a pollution map. The traffic pollution mapper may utilize various sensors to detect pollution, including automotive AQSs that provide binary open and close signals.

19 Claims, 4 Drawing Sheets

(51) Int. Cl.
   *G01N 33/00*   (2006.01)
   *H04W 4/44*   (2018.01)

(56) References Cited

U.S. PATENT DOCUMENTS

| | | | |
|---|---|---|---|
| 5,725,425 | A | 3/1998 | Rump et al. |
| 6,104,299 | A | 8/2000 | Brusseaux et al. |
| 6,206,775 | B1* | 3/2001 | Lemaitre .............. B60H 1/008 |
| | | | 139/158 |
| 7,603,138 | B2 | 10/2009 | Zhang et al. |
| 7,857,892 | B2 | 12/2010 | Marra |
| 7,900,501 | B2 | 3/2011 | Moseley |
| 8,171,136 | B2 | 5/2012 | Petite |
| 8,515,614 | B2 | 8/2013 | Bernard |
| 8,744,766 | B2 | 6/2014 | Rakshit |
| 8,903,646 | B2 | 12/2014 | Althen et al. |
| 9,111,240 | B2 | 8/2015 | Petite |
| 9,141,094 | B2 | 9/2015 | Pariseau et al. |
| 9,766,993 | B2* | 9/2017 | Agrawal ................ H04L 67/12 |
| 2002/0107634 | A1 | 8/2002 | Luciani |
| 2008/0024323 | A1 | 1/2008 | Kadaba |
| 2008/0033644 | A1 | 2/2008 | Bannon |
| 2008/0041138 | A1* | 2/2008 | Marra ................ G01N 1/2205 |
| | | | 73/31.02 |
| 2011/0251800 | A1* | 10/2011 | Wilkins .................... G01J 3/02 |
| | | | 702/24 |
| 2012/0293315 | A1* | 11/2012 | Schunder ......... G08G 1/096775 |
| | | | 340/438 |
| 2013/0080053 | A1* | 3/2013 | Rakshit ............. G01C 21/3461 |
| | | | 701/527 |
| 2014/0032175 | A1* | 1/2014 | Agrawal ................ H04L 67/12 |
| | | | 702/189 |
| 2015/0212057 | A1 | 7/2015 | Darveau |
| 2016/0101682 | A1* | 4/2016 | Choi .................... B60K 11/085 |
| | | | 701/36 |
| 2016/0133068 | A1* | 5/2016 | Chu ..................... G07C 5/0808 |
| | | | 701/33.2 |

FOREIGN PATENT DOCUMENTS

| | | | | |
|---|---|---|---|---|
| CN | 20142496531 | | 1/2015 | |
| DE | 2000143797 | | 2/2004 | |
| EP | 1190879 | | 3/2002 | |
| EP | 1422089 | * | 11/2003 | ......... B60H 1/00849 |
| FR | 20110061342 | | 6/2013 | |
| JP | 19980125389 | | 11/1999 | |
| JP | 20080146635 | | 12/2009 | |
| KR | 20060035066 | | 10/2007 | |
| KR | 20070034588 | | 10/2008 | |
| KR | 20070082776 | | 2/2009 | |
| KR | 20100131285 | | 6/2012 | |
| WO | WO2001EP09783 | | 2/2004 | |
| WO | WO-2015159101 A1 | * | 10/2015 | ......... G01N 33/0075 |

OTHER PUBLICATIONS

Thomas Tille, Automotive Requirements for Sensors using Air Quality Gas Sensors as an Example, Sep. 5, 2010 (Year: 2010).*

Thomas Tille. Automotive Requirements for Sensors using Air Quality Gas Sensors as an Example, 2010, Published by Elsevier Ltd. (Year: 2010).*

Karin Tuxen-Bettman, Making the invisible visible by mapping air quality, Google Green Blog, Sep. 2015, http://googlegreenblog.blogspot.com/2015/09/making-invisible-visible-by-mapping-air.html (retrieved May 23, 2016).

Donnay, Albert, Potential for mapping minute-to-minute carbon monoxide and nitrogen dioxide measurements collected bymillions of mobile sensors deployed worldwide, 2013, http://www.academia.edu/14237908/Donnay_poster_on_CO_NO2_sensors_in_vehicles_from_EPA_Air_Sensors 2013.

* cited by examiner

TRAFFIC POLLUTION MAPPER

CROSS-REFERENCE TO RELATED APPLICATION

This application claims priority to U.S. Provisional Patent Application No. 62/308,966, filed Mar. 16, 2016.

BACKGROUND OF THE INVENTION

Field of the Invention

The invention relates to traffic pollution and in particular to systems and methods combining air quality sensors, location information, and wireless communication, to establish pollution maps and statistics.

Related Art

Traffic pollution is typically a complex mixture of particles of various sizes, and gases. Gases present in traffic pollution are often categorized by, reducing gases, such as carbon monoxide (CO), volatile organic compounds (VOCs) and hydrocarbons (HCs), and oxidizing gases, such as nitrogen oxides (NOX).

Air Quality Sensors (AQS) modules have been assembled on high end European commercial automobiles since the late 1980s. These AQS modules are now used on a large number of mid-range European and Asian car models. AQS modules are sold by several European and Asian companies to tier one automotive suppliers or OEMs for factory installation during car assembly. They are usually installed outside the cabin, close to a cabin air intake, or even around the front bumper area. They are often based on dual sensors. One sensor detects the reducing gases (VOCs HCs, etc.,) and the other one detects the oxidizing gases (NOX etc. . . . ). These AQS modules communicate with the car air conditioning (AC) system and issue recommendations to the AC processor to close the recirculation flap when the pollution is high, to keep the polluted air outside the cabin. When the air pollution decreases, an AQS module recommends the AC system to reopen the flap, to let some fresh air into the cabin. No indication is however usually given to the user as to when the flap is opened or closed.

Use of semiconductor gas sensors, such as AQS modules, in vehicles has been documented. For instance, the following references describe various traffic pollution sensing, pollution information collection and transmission, and pollution mapping systems and methods.

U.S. Pat. No. 9,111,240 describes a system for transmitting pollution information over an integrated wireless network.

U.S. Pat. No. 6,104,299 describes a device for monitoring pollution caused by motor vehicles in an urban area.

U.S. Pat. No. 8,903,646 describes a method for determining emission locations.

Patent Application Nos. DE2000143797 20000906 and WO2001EP09783 20010824 describe an integrated traffic monitoring system.

Patent Application No. CN20142402720U 20140721 (page bookmark CN204109933) describes an intelligent detection device for gases inside car based on ZIGBEE.

Patent Application No. CN20142496531U 20140829 (page bookmark CN204095738 (U)) describes an in-car air pollution monitoring device Patent Application No. CN20121590228 20121229 (page bookmark CN103901162 (A)) describes a portable in-car gas detection system and method.

Patent Application No. KR20100131285 20101221 describes a mood lamp using indoor pollution display of vehicle and indoor pollution display method using the same.

Patent Application No. KR20070082776 20070817 describes a car audio displaying air pollution and the control method thereof.

Patent Application No. KR20070034588 20070409 describes a method for enhancing an Air Quality Sensor function by displaying information to user.

Patent Application No. KR20060035066 20060418 describes a system for measuring level or air pollution inside car.

Patent Application No. JP19980125389 19980421 describes an instrument and method for measuring traffic volume based on pollution.

Patent Application No. FR20110061342 20111208 describes a method for calculating unpolluted route for road navigation system in car.

Patent Application No. JP20080146635 20080604 describes a vehicle information device that controls air intake based on pollution map data communicating directly with car air conditioning system.

From the discussion that follows, it will become apparent that the present invention addresses the deficiencies associated with the prior art while providing numerous additional advantages and benefits not contemplated or possible with prior art constructions.

SUMMARY OF THE INVENTION

A traffic pollution mapper that collects pollution information and generates pollution maps (among other things) is disclosed herein. The traffic pollution mapper may include pollution detectors in a large number of vehicles driving in traffic or elsewhere. These pollution detectors may utilize or include existing automotive AQSs already installed in mid-range to high-end vehicles, or may include their own pollution sensors.

The traffic pollution mapper can provide real time traffic pollution maps, which can be used by users to better understand the traffic pollution they are exposed to, and minimize their exposure. This is particularly useful to more sensitive population groups like asthmatics, babies and the elderly. Users may also plan their routes in light of pollution maps provided by the traffic pollution mapper. In addition, pollution maps can be used by routing and navigation companies to complement their products, or by city or state planning departments to improve the road network and minimize pollution "hot spots." Pollution maps can be also used by air quality institutions to better understand pollution patterns, such as times and places when/where pollution is high or low or therebetween.

Various embodiments of a traffic pollution mapper are disclosed herein. For instance, in one exemplary embodiment, a traffic pollution mapper for a plurality of vehicles is disclosed, with such traffic pollution mapper comprising a plurality of pollution detectors, a plurality of client devices and one or more remote servers.

The plurality of pollution detectors is each attached to a vehicle. Also, each of the pollution detectors comprises one or more sensors that detect one or more changes in pollution levels and generate pollution information based on the changes in pollution levels, and one or more communication devices that transmit the pollution information. The pollution information may comprise one or more binary open or close signals, such as from an automotive AQS, that open or close a recirculation flap.

The plurality of client devices is each associated with at least one of the plurality of pollution detectors. Each of the plurality of client devices comprises a communication device that receives the pollution information, a location device that determines a location of the vehicle, a clock that generates one or more timestamps, and one or more processors that generate mapping information including the pollution information, the location and the timestamps.

The remote servers comprise one or more processors and one or more storage devices, wherein the remote servers receive the mapping information from the communication device of the plurality of client devices and store the mapping information in the storage devices.

The mapping information in the storage devices may be accessible by one or more of the plurality of client devices via the remote servers. The remote server may also generate one or more pollution maps based on the mapping information, the pollution maps comprising a map having pollution information from the mapping information associated with various locations on the map.

It is noted that each of the plurality of client devices may comprise a screen that presents the pollution information received at its communication device. Also, client devices may present an alert when the pollution information indicates a change in pollution beyond a particular threshold. The pollution information may be transmitted to each of the plurality of client devices via one or more first wireless communication links, and the mapping information may be received by the servers via one or more second wireless communication links.

In another exemplary embodiment, a traffic pollution mapper for one or more vehicles is disclosed, comprising a software application and one or more servers. One or more pollution detectors detect pollution variations and output pollution information based on the pollution variations. The pollution detectors are factory-installed in the vehicles. The pollution information may comprise one or more binary open and close signals, such as from an automotive AQS, that open or close a recirculation flap.

The software application is stored on a non-transitory storage medium and, when executed by one or more client devices, causes the client devices to receive the pollution information from at least an associated one of the pollution detectors, generate mapping information comprising the pollution information, location information generated by a location device, and a timestamp, and transmit the mapping information to a server. The software application may also cause each of the client devices to present pollution information on a screen of each of the client devices.

The servers receive and store the mapping information. It is noted that the servers may provide access to the mapping information stored thereon upon receipt of a request for the mapping information by the client devices. The one or more servers may generate one or more pollution maps based on the mapping information, the pollution maps comprising a map having pollution information from the mapping information associated with various locations on the map.

The pollution information may be wirelessly transmitted to the client devices by the pollution detectors, while the mapping information may be received by the servers via a wireless communication link between the servers and the client devices.

Various methods relating to pollution detection and mapping are disclosed herein as well. For instance, in one exemplary embodiment a method for generating and using a traffic pollution map is disclosed, with such method comprising detecting pollution and generating pollution information at a plurality of pollution detectors, wherein each pollution detector is installed at a vehicle, generating mapping information comprising the pollution information, location information, and a timestamp, and receiving the mapping information at one or more servers. The pollution information may comprise one or more binary open and close signals, such as from an automotive AQS.

The method also includes storing the mapping information at one or more storage devices after the mapping information is received by the servers receiving one or more requests for one or more subsets of the mapping information stored at the storage devices from one or more client devices, and transmitting one or more subsets of mapping information to the client devices in response to the requests.

One or more pollution maps may be generated based on the mapping information. The one or more pollution maps will typically comprise a map having pollution information associated with various locations on the map.

A software application that is executable by one or more client devices may be provided as well. When executed the software application typically causes the client devices to receive the pollution information from the pollution detectors and display the pollution information on a screen of the client devices. The software application may also cause the client devices to generate the mapping information with location information generated by a location device of a client device. Alternatively or in addition, the pollution detectors may include a location device and the pollution detectors may generate the mapping information with location information generated by the location device.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In one or more embodiments, the traffic pollution mapper comprises a combination of elements that build traffic pollution databases that may be used to link pollution information to location, date and time. This linked information will be referenced herein as a pollution map. A pollution map may be updated in real time and therefore provide information on the real time evolution of pollution. In addition, pollution maps over time may be used to track pollution variations and trends. Pollution maps can also be used to predict pollution patterns on any given day and time.

In addition, pollution maps may be made available to various users, such as to help them understand their exposure to pollution and plan their routes. For example, a pollution map may complement routing and navigation tools provided by companies such as GOOGLE, GARMIN and TOMTOM.

Figure 1:
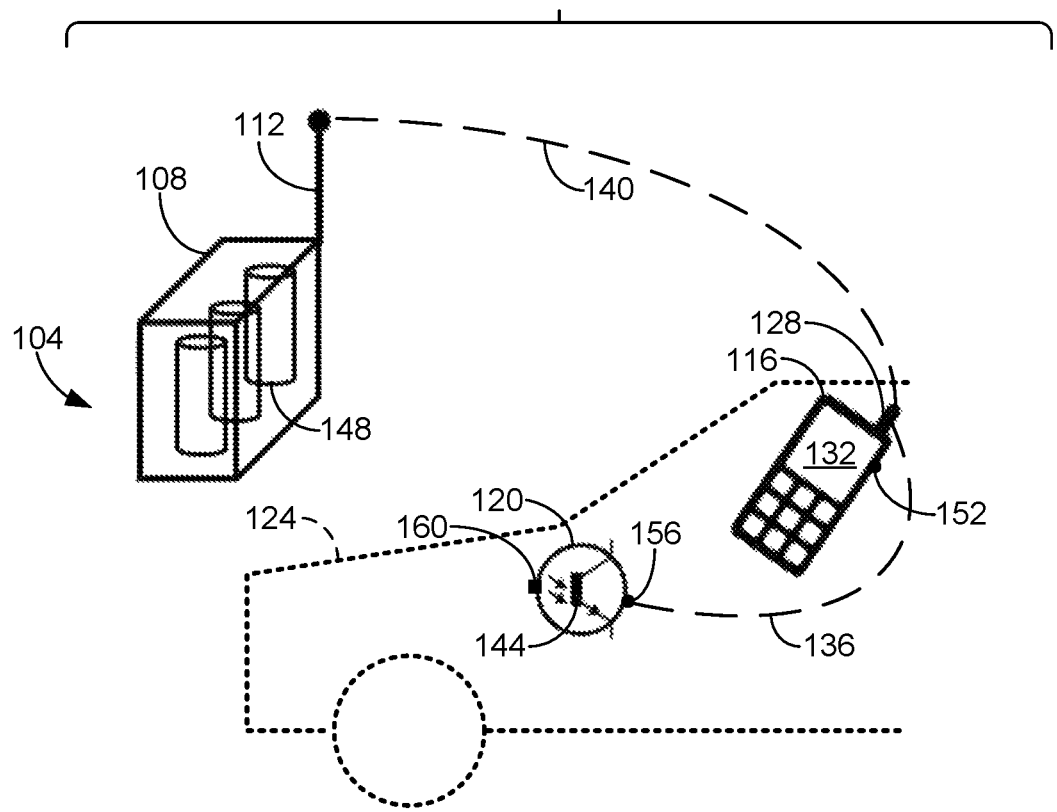
FIG. 1 is a block diagram illustrating an exemplary traffic pollution mapper.

FIG. 1 illustrates an exemplary traffic pollution mapper 104. As can be seen, a traffic pollution mapper 104 may comprise one or more pollution detectors 120, one or more client devices 116, and one or more servers 108. Typically, a pollution detector 120 and at least one client device 116 are associated (i.e., in communication with one another) and located in the same vehicle 124. The pollution detector 120 and client device 116 in a vehicle communicate with one another and the client device communicates with a remote server 108. In this manner, information regarding pollution collected at the vehicle 124 at various locations can be gathered at the remote server 108 for processing, storage or other disposition as will be described further below. A plurality of associated pollution detectors 120 and client devices 116 may be deployed in a plurality of vehicles 124 to gather information regarding pollution from many locations simultaneously.

A pollution detector 120 detects variations of pollution in the air coming into a vehicle cabin via one or more pollution sensors 144 and outputs pollution information based on the same. Pollution information may also or alternatively include absolute levels of pollution detected by a pollution detector.

In one or more embodiments, a pollution detector 120 may include at least two pollution sensors 144 to detect various types of pollution (i.e., various gas and particular concentrations). For example, a first pollution sensor 144 may detect gasoline pollution, such as reducing gases such as carbon monoxide (CO), hydrocarbons (HC) and VOCs, while a second pollution sensor detects diesel pollution, such as oxidizing gases like nitrogen oxides (NO2). It is noted that a single pollution sensor 144 may detect one or more types of pollution.

A pollution sensor 144 may be a semiconductor gas sensor, such as an automotive AQS, that measures only relative changes in aggregate pollution concentrations or levels, but may also be a more expensive and selective sensor that measures absolute pollutant concentrations or levels (e.g., gas concentrations in parts per million or parts per billion). Pollution sensors 144 may also be various other chemical sensors that detect pollutants. Pollution sensors 144 may have a periodic sampling rate, such as several times per second.

It is noted that pollution sensors 144 capable of detecting absolute levels of pollution are more complex and less cost effective. Therefore, one advantage of the traffic pollution mapper 104 is that it is capable of using less expensive and more commonplace sensors, such as automotive AQSs, to provide the functionality disclosed herein. It is noted that detecting pollution variations or peaks, as an automotive AQS does, is advantageous in that it is cheaper and easier to achieve technically than detection of absolute pollution levels. In traffic, high pollution variations, or peaks, are very well correlated to locally high absolute pollution levels.

Typically, a pollution detector 120 will be a standalone device installed in a vehicle 124 that houses its own pollution sensor(s) 144. A standalone pollution detector 120 may be a self-contained device clipped or otherwise attached at a vehicle's air vent via a mount 160. For example, a standalone pollution detector, such as the "traffic pollution indicator" disclosed in U.S. Provisional Patent Application No. 62/239,940 and U.S. patent application Ser. No. 15/148,637, both incorporated herein by reference, may be installed inside a vehicle cabin, such as at an air vent, to provide pollution information to a client device for presentation to a user.

Alternatively, a pollution detector 120 may comprise an automotive AQS (used as a pollution sensor 144) installed in a vehicle 124 by the vehicle's OEM. It is contemplated that an automotive AQS or other pollution sensor 144 may be positioned at various locations, such as at a cabin air intake, inside the car cabin, at an air vent or in a pollution detector 120 installed in or attached to a vehicle.

Pollution information may be shared with various other devices by a pollution detector 120. As can be seen from FIG. 1 for example, a pollution detector 120 may communicate pollution information via one or more first communication links 136. It is contemplated that a first communication link 136 may be wired (e.g., USB) or wireless (e.g., BLUETOOTH, ZIGBEE). Typically, pollution information will be communicated with a client device 116, such as a smartphone, tablet, computer or other computing device.

A client device 116 will typically comprise a screen or display 132 and one or more communication devices 128. A location sensor 152, such as a GPS receiver, may also be included. A client device 116 may receive pollution information from a pollution detector 120 via a communication link 136 with the pollution detector that is established by the client device's communication device 128. A client device 116, may also present pollution information from a pollution detector on its display 132.

Mapping information comprising pollution information, location information or both, along with a timestamp (or various subsets thereof) may be generated and communicated to one or more servers 108 by a client device 116. As can be seen, one or more second communication links 140 may be established between a communication device 112 of a server and a communication device 128 of a client device 116 to facilitate such transfer of pollution information. A second communication link 140 will typically be wireless (e.g., cellular).

It is noted that a first communication link 136 may be a local communication link established to effectuate communications within a short range, such as within a vehicle 124. A second communication link 140 may have a longer range to allow mapping information to be shared with a server 108 that is remote from a pollution detector 120 and its associated vehicle 124. A client device 116 may comprise a plurality of individual communication devices 128 to establish separate communication links 136, 140.

Typically, a server 108 will receive mapping from a plurality of pollution detectors 120. To illustrate, in a widespread deployment, a server 108 may receive information from individual pollution detectors 120 in a thousands or even millions of vehicles. This is advantageous in generating a map of pollution at various locations for various periods of time. As disclosed above, pollution information may first be transmitted to a client device 116, which then transmits the pollution information to a server 108.

A server 108 may process mapping information to establish statistical pollution information, such as pollution maps showing pollution information in relation to location, pollution variations showing how the pollution varies over time in one or more particular locations, and various combinations of the foregoing. A server 108 may also store the mapping information, such as on one or more data storage devices 148.

It is noted that a server 108 may also provide access to mapping information. For example, a server 108 may comprise a web server, database server or other hosting service that can be accessed by users via the internet or other network. Users may use this information for various reasons, including to choose less polluted routes, pick a better time to travel, adjust their driving behavior, close their vehicle's recirculation flap in highly polluted areas, or simply to obtain pollution information they are interested in.

Figure 2:
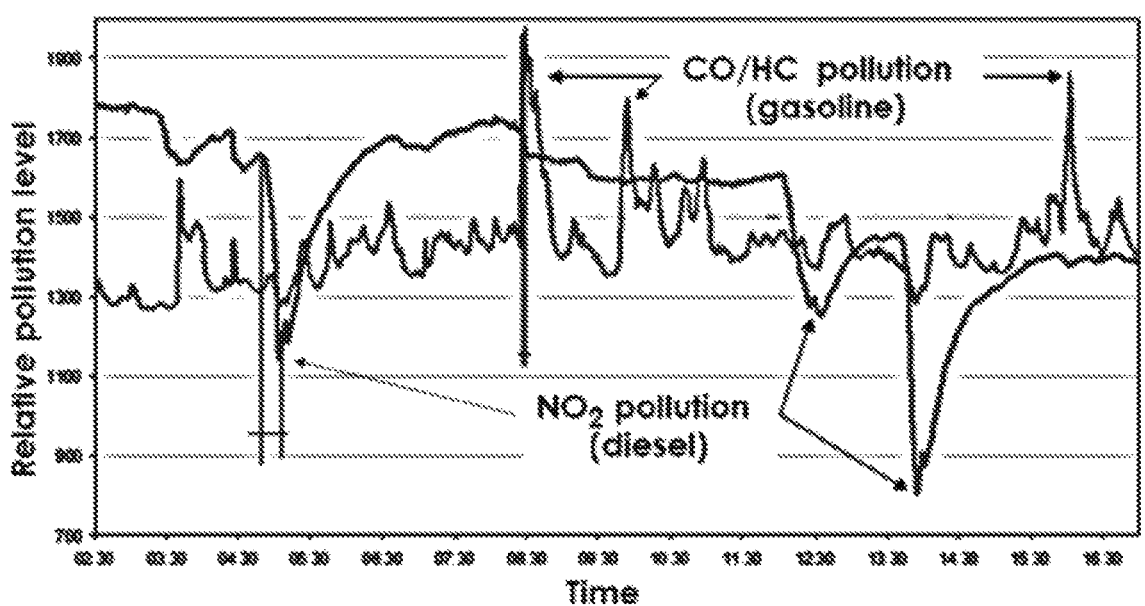
FIG. 2 illustrates a graph of exemplary pollution information.

FIG. 2 provides an example of pollution information captured by a pollution detector. Specifically, FIG. 2 provides a graph of sensor information showing variations in pollution levels over approximately 12 minutes. The vertical scale is a relative scale and does not translate into absolute gas concentrations. Instead, the vertical scale shows relative changes of aggregate pollution levels over time. The curve labelled "NO2" shows variations of aggregate oxidizing gases, including nitrogen dioxide. The curve labelled "CO/HC" shows variations of aggregate reducing gases, including carbon monoxide and hydrocarbons.

Figure 3:
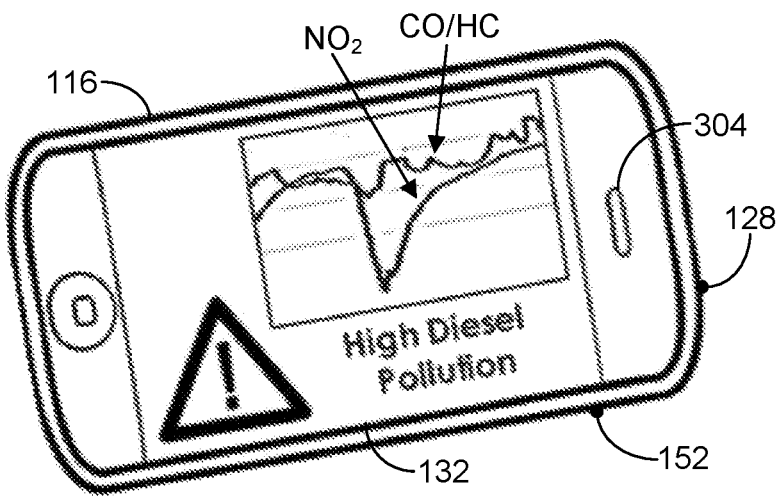
FIG. 3 illustrates an exemplary client device.

FIG. 3 illustrates an exemplary client device 116 having a display 132 presenting pollution information. Here, the pollution information comprises a portion of a real time pollution information plotted on two curves, labeled "CO/HC" and "NO2." In addition, an alert regarding a diesel pollution peak is presented on the display 132. It is noted that, rather than visual output, an alert for a pollution peak may also be a sound, a spoken message or other audible output played via a speaker 304. In this manner, information can be spoken by a client device instead of displayed, in a similar manner as it is done by a navigation system, so that even a driver can benefit from it, without having to look at a display 132.

Figure 4:
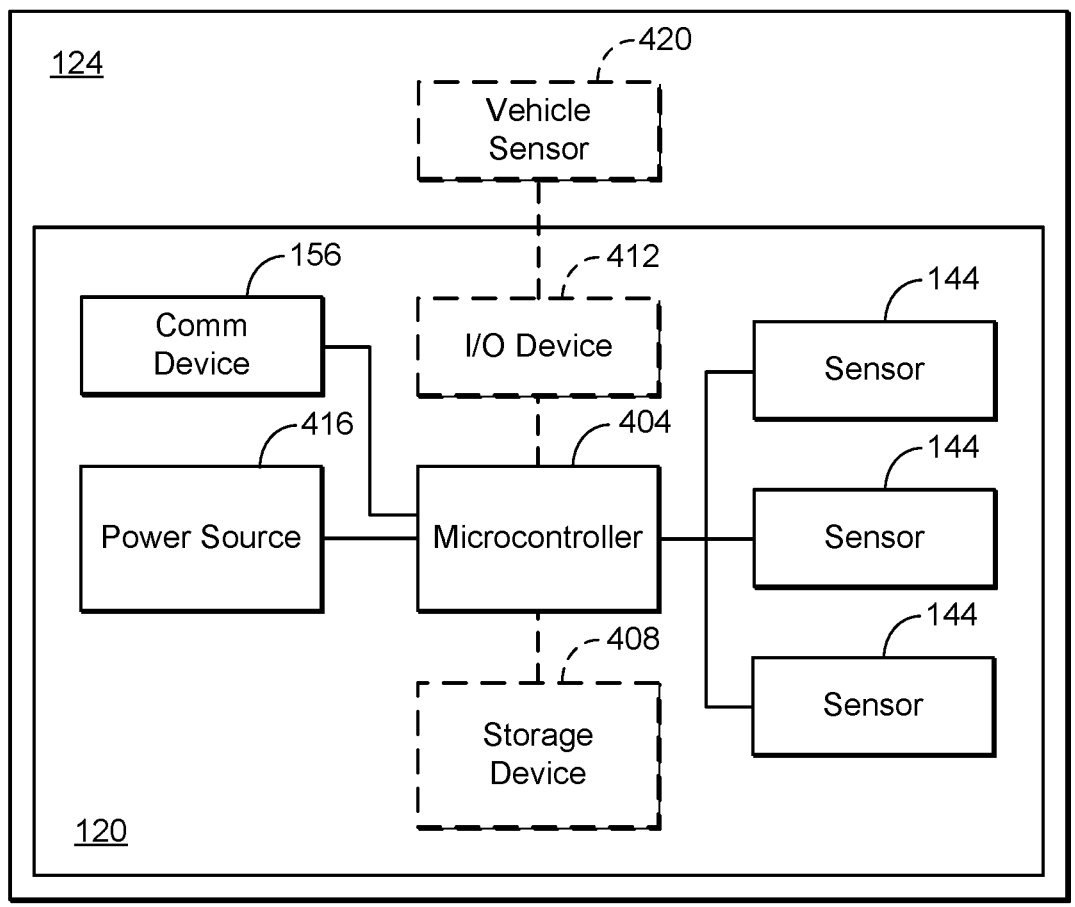
FIG. 4 is a block diagram illustrating components of an exemplary pollution detector.

FIG. 4 is a block diagram illustrating an exemplary pollution detector 120 and components thereof. As illustrated, the pollution detector is in a vehicle 124 but may be mounted on an exterior of the vehicle if desired. A pollution detector 120 may comprise one or more microcontrollers 404 and one or more pollution sensors 144. A microcontroller 404 may be a processor, circuitry or the like that controls operation of the pollution detector 120. A microcontroller 404 may execute one or more instructions, such as in the form of machine readable code comprising one or more instructions that provide the pollution detector's functionality as disclosed herein. It is contemplated that machine readable code may be stored in a storage device 408 or hardwired in a microcontroller 404. A storage device 408 may optionally be a separate component, such as shown, or may be integrated into a microcontroller.

As an option, a pollution detector may include and execute instructions, similar to that of existing automotive AQS modules installed on millions of vehicles. These instructions output a binary signal to a recirculation flap of a vehicle, recommending whether the flap should be opened or closed. In general, a close signal recommends the flap be closed when a sufficiently high pollution peak is detected. An open signal recommends the flap be opened when the pollution level goes back down. It is contemplated that these instructions can also or alternatively be executed by a processor of a client device.

As disclosed above, a pollution sensor 144 may be various kinds of sensors. Some exemplary types of sensors include, chemical sensors and automotive AQS and other semiconductor sensors. A particular pollution sensor 144 may be capable of detecting a change in concentration/level or absolute level of one or more pollutants (i.e., pollution information). Also, as disclosed above, a pollution detector 120 may comprise a plurality of pollution sensors 144, with each pollution sensor being sensitive to different pollutant(s).

A pollution detector 120 may optionally utilize an existing vehicle pollution sensor 420, such as a vehicle's AQS. In such case, an I/O device 412 may be provided to communicate with the vehicle pollution sensor 420 via a wired or wireless connection. An I/O device 412 may relay information received from a vehicle pollution sensor 420 to a microcontroller 404 for processing. It is contemplated that a microcontroller 404, I/O device 412 or both may include an analog to digital converter, where vehicle pollution sensors 420 or internal pollution sensors 144 provide pollution information as analog output. Alternatively, one or more separate analog to digital converter components may be included for such purposes.

It is noted that some automotive AQSs may only output a binary open or close signal, such as the flap open or close signal discussed above. In such cases, it is contemplated that pollution information may include this binary signal in addition or instead of a change in pollution levels or an absolute pollution level reading.

One or more communication devices 156 may be provided to facilitate communication with other elements of a traffic pollution mapper. As disclosed with regard to FIG. 1 for instance, a communication device 156 may provide a communication link with a client device 116 and communicate information therewith. A communication device 156 may provide a wired or wireless communication link.

One or more power sources 416 may also be included in a pollution detector 120. Some exemplary power sources 416 include batteries and solar panels. Alternatively or in addition, it is contemplated that a pollution detector 120 may utilize an external power source, such as a vehicle to power its operation or charge internal power sources. For example, a pollution detector 120 may be attached to a cigarette lighter, USB port or other outlet of a vehicle 124 to receive power therefrom.

A pollution detector may be clipped or attached to a vehicle 124, such as at an air vent of the vehicle. In operation, a pollution detector 120 detects variations of pollution in the air coming into the cabin (i.e., pollution information). For example, at least a first and second pollution sensors 144 of the pollution detector 120 may be provided to respectively detect gasoline pollution (reducing gases such as Carbon monoxide, Hydrocarbons, VOCs) as well as diesel pollution (mainly oxidizing gases such as nitrogen oxides). The pollution information may be communicated to an external device, such as a client device, via a communication device 156.

Figure 5:
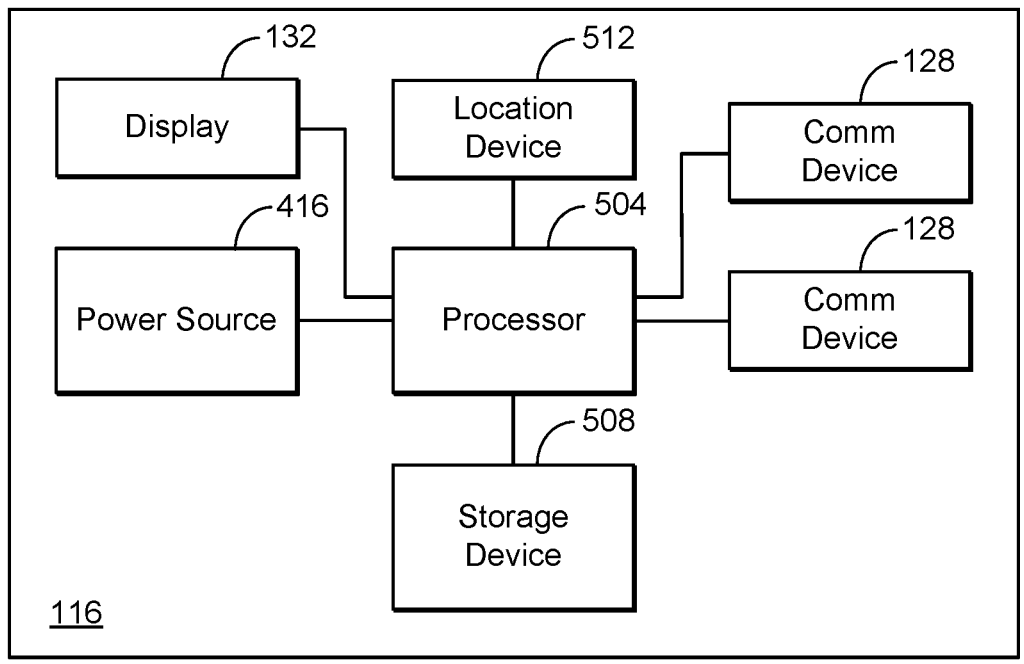
FIG. 5 is a block diagram illustrating components of an exemplary client device.

FIG. 5 is a block diagram illustrating an exemplary client device 116 and components thereof. As can be seen, a client device 116 may comprise one or more processors 504, one or more storage devices 508, one or more communication devices 128, and one or more displays 132. Some exemplary client devices 116 include smartphones, tablets, and computers. Other computing devices may be used as client devices 116 as well.

A client device's processor 504 may execute a software application or machine readable code comprising one or more instructions stored on a storage device 508 to provide the functionality disclosed herein. For instance, the application may cause a client device 116 to receive pollution information from a pollution detector at the client device's communication device 128. The application may also instruct a client device 116 to display pollution information on its display device 132. For example, a processor 504 may execute the application to generate a visual representation of pollution information, such as a graph or numerical representation of pollution information. In addition, the application may trigger an alert, such as described with regard to FIG. 3, when particular pollution information changes beyond a predefined threshold. A software application, when executed, may also cause a client device 116 to receive pollution information, generate mapping information and communicate mapping information with a server 108.

A location device 512, such as a GPS receiver, may be included as well. A location device 512 determines the location where pollution information is being captured. The speed and heading of a vehicle's motion may also be captured. This location information can be communicated along with pollution information to a server for pollution mapping purposes. In addition, location information may be used to retrieve a pollution map for a particular area from a server. For example, a pollution map for the current location may be obtained by a client device 116 sending a request to a server including location information identifying the current location. Thereafter, the pollution map can be presented on a display 132 of a client device 116.

Figure 6:
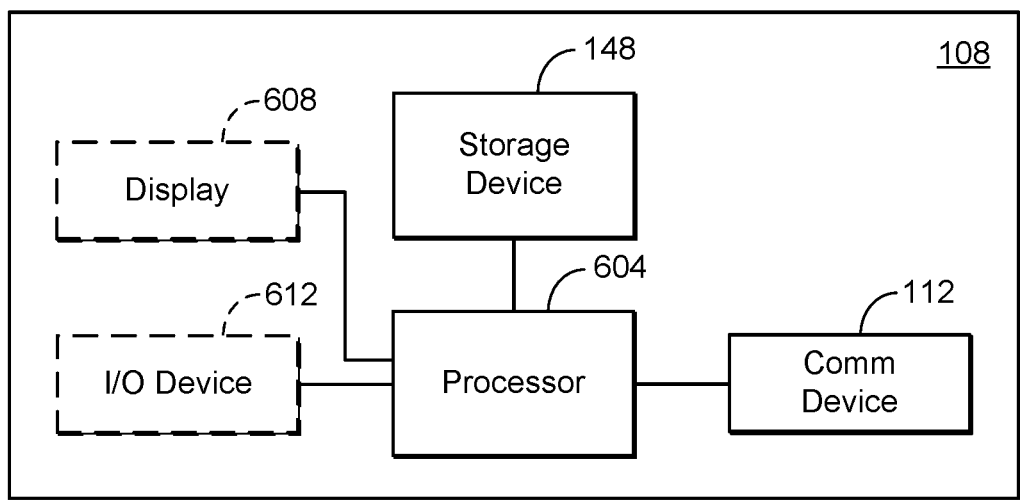
FIG. 6 is a block diagram illustrating components of an exemplary server.

FIG. 6 illustrates an exemplary server 108 and components thereof. As can be seen, a server 108 may comprise one or more processors 604, one or more communication devices 112, and one or more storage devices 148. A processor 604 may execute machine readable code comprising one or more instructions to provide the server functionality disclosed herein. Machine readable code may be stored on a storage device 148. Alternatively, a processor 604 may be hardwired with such instructions. A server 108 may optionally comprise one or more displays 608 and I/O devices 612 (e.g., keyboard, pointing device, speaker, and other human interface devices) such as to allow an operator or administrator to control operation of the server.

In operation, a server 108 may communicate with one or more client devices with its communication device(s) 112, such as to receive pollution information or mapping information therefrom. Typically, a server 108 will communicate with a plurality of client devices to establish a pollution map. A server 108 may also provide hosting services, such as a web server or database server through which mapping information, pollution information, pollution maps or other information can be retrieved.

Figure 7:
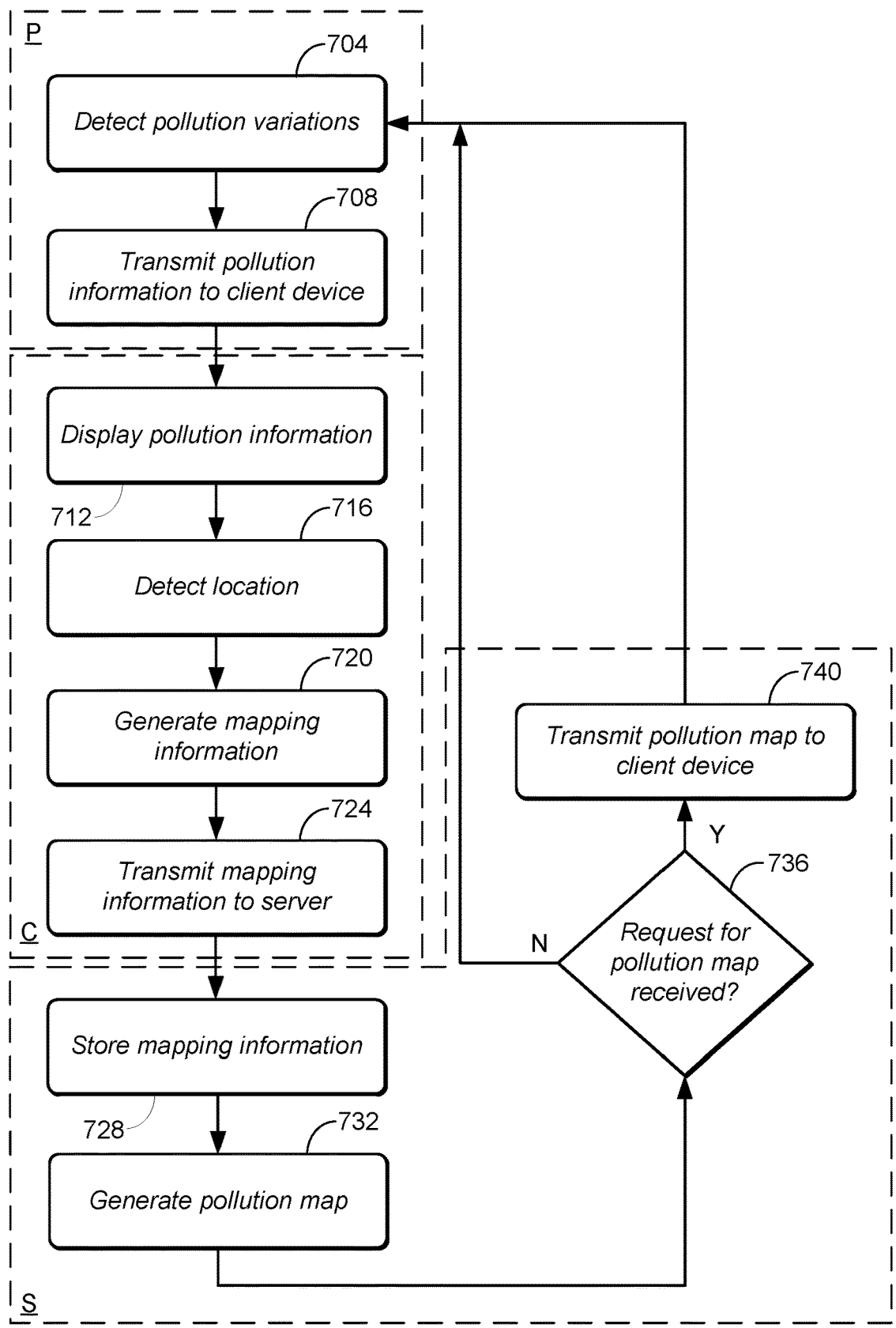
FIG. 7 is a flow diagram illustration operation of an exemplary traffic pollution mapper.

Further details regarding the operation of a traffic pollution mapper and elements thereof will now be described with regard to FIG. 7. Though various steps of the operation may be performed by various components of the traffic pollution mapper, in FIG. 7, the dashed boxes labeled P, C, and S respectively indicate steps performed by the pollution detector, client device, and server of the traffic pollution mapper.

At a step 704, one or more pollution levels or pollution level changes may be detected by one or more sensors of a pollution detector. Typically, a pollution detector will generate pollution information with pollution information representing a change in pollution levels (for one or more types of pollution) or absolute levels of pollution. The pollution information may then be transmitted from a pollution detector to one or more client devices via a communication link at a step 708.

At a step 712, the client device may execute an application to receive the pollution information and generate a visual representation thereof, such as shown and described with regard to FIG. 3. At a step 716, the client device may detect its current location with a location device. Mapping information including the pollution information, location information detected by the location device, and a timestamp may be generated by the client device at a step 720. At a step 724, the mapping information may be transmitted to a server via a communication device of the client device.

Mapping information may be stored on a storage device of a client device in some embodiments. For example mapping information may be recorded approximately every second by a client device. Mapping information may be sent in real time to the server, but if communication with the server is not available, storage of mapping information allows transmission to be delayed until communication is possible.

As an option, a client device can also perform more processing on mapping information such as computing pollution levels or counting the number of pollution events. This processed information can also be sent to the server.

The server will typically receive mapping information (or a subset thereof) from thousands or millions client devices. The mapping information may be stored in a storage device of the server at a step 728. The mapping information may be stored in a database or the like in the storage device.

Using the mapping information, at a step 732 the server may generate one or more pollution maps showing how often pollution peaks occur and how high pollution peaks are in particular areas. It is noted that the mapping information will typically be weighted by the number of client devices reporting mapping information for a particular area. For example, if ten pollution peaks are detected in an area over 5 minutes where one hundred client devices are present, that will indicate a much lower pollution peak density than if a hundred pollution peaks are detected over 5 minutes in an area where only ten client devices are present.

A server may use, among other things, the following data to generate a pollution map: number of client devices present or passing through an area, pollution peak amplitudes, number of pollution peaks, frequency of pollution peaks, types of pollution (e.g., gasoline or diesel or both), flap closure binary signal (open or close), location, date, and time.

In one or more embodiments, a pollution map comprises a map where pollution variations or peaks are associated with roadways, their frequency, the number of times a recirculation flap closure signal or recommendation was issued, the time of day when they are the highest, the type of pollution, the dates when the pollution is high or low etc. . . .

Once the database has collected enough mapping information to be statistically significant, users may be permitted to consult the database, such as to download pollution maps or retrieve data from the database directly. At a decision step 736, if a request is received by the server, a pollution map may be transmitted to the client device that made the request at a step 740. A request may include location information specifying one or more areas for which mapping information or a pollution map is desired.

Mapping information and pollution maps can be used to understand the distribution of pollution over an area of interest, plan user travel routes based on the pollution information, and to reduce user exposure to pollution. This can have positive effects in terms of health and productivity. A client device may be used to access the database via a communication link or network connection, such as the internet.

Thereafter, the retrieved information or map may be displayed on a display of a client device to users in a vehicle. In general, information displayed by the client device to the users in the vehicle includes:

(A) The pollution information collected from sensors of a pollution detector. This pollution information can include: filtered sensor signal graphs showing the actual variations in pollution, alert messages telling the user when significant pollution is detected, recirculation flap opening and closing recommendations, voice messages, etc. . . .

(B) The information, such as pollution map, mapping information or other data, retrieved from the server. This information can be displayed as an actual map similar to the maps displayed by navigation devices. Pollution levels may be color coded on that map in a similar way as it is done on navigation maps for traffic density. A user may access this data whether the user is in a vehicle or not, such as to plan a less polluted route and therefore minimize exposure to pollution.

A traffic pollution mapper may operate continuously to collect pollution information. As shown in FIG. 7, operation may repeatedly return to step 704, where pollution levels are detected, to continuously collect pollution information.

In an alternate embodiment of the invention, a pollution detector need not be provided. Instead, a vehicle's existing AQS may communicate pollution information directly with a client device, and the client device displays the pollution information and transmits the pollution information to a server, or both.

In another alternate embodiment, no AQS or pollution detector is onboard a vehicle (whether they are provided by the vehicle's manufacturer or by the user). In such embodiments, pollution maps data from a server may be used to reduce the pollution in the vehicle's cabin by closing and re-opening a recirculation flap as if the vehicle had an onboard AQS.

To illustrate, a server may issue a recirculation flap closure instruction or signal when the vehicle drives through a highly polluted area, or typically highly polluted area as indicated by mapping information stored by the server. A client device receives this instruction and sends it to one of the vehicles central processing units (CPUs), such as its air conditioning CPU. The air conditioning CPU executes the flap closure instruction and closes the flap.

Mapping information and pollution maps collected/generated by a traffic pollution mapper can therefore contribute to reducing the pollution in the cabin in a similar manner as an onboard AQS. This would be very cost effective as no specific hardware is needed in the car. To implement the above flap control based on pollution maps, manufacturers may need to work with a traffic pollution mapper provider to be able to exchange the data and use it appropriately.

In another alternate embodiment, a vehicle itself may have its own communication device to access mapping information or pollution maps from a server, such as to display a pollution map, or control its recirculation flap without the need for a client device or AQS. Pollution information, mapping information or a pollution map may be displayed via the vehicle's display. The vehicle's speakers can also output the audible messages and alerts instead of a client device. If the vehicle does include an AQS, pollution information therefrom can be displayed and communicated by the vehicle itself, without need for a client device.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A traffic pollution mapper for controlling one or more recirculation flaps at a plurality of vehicles comprising:
   a plurality of pollution detectors for a subset of the plurality of vehicles, each attached to a vehicle of the subset and comprising one or more sensors that detect pollution information consisting of relative changes in pollution with time, and one or more communication devices that transmit the pollution information;
   a plurality of client devices, each associated with at least one of the plurality of pollution detectors, each of the plurality of client devices comprising a communication device that receives the pollution information, a location device that determines location information for the vehicle, and a clock that generates one or more timestamps; and
   one or more remote servers comprising one or more processors and one or more storage devices, wherein the one or more remote servers receive and store the pollution information, the location information, and the one or more timestamps from the plurality of client devices, generate one or more pollution maps associating pollution levels with one or more locations and one or more times based on the relative changes in pollution with time, the location information, and the one or more timestamps, and transmit the one or more pollution maps to the plurality of vehicles;
   wherein the one or more recirculation flaps are closed or opened based on the one or more pollution maps transmitted to the plurality of vehicles by the one or more servers to reduce exposure to pollution in the plurality of vehicles, including one or more vehicles outside the subset;
   wherein the one or more vehicles outside the subset are not involved in detecting the pollution information.

2. The traffic pollution mapper of claim 1, wherein the pollution information comprises one or more binary recirculation flap open or close signals for purposes of generating the one or more pollution maps.

3. The traffic pollution mapper of claim 1, wherein each of the plurality of client devices further comprises a screen that presents the pollution information received at its communication device.

4. The traffic pollution mapper of claim 1, wherein each of the plurality of client devices presents an alert when the pollution information indicates a change in pollution beyond a particular threshold.

5. The traffic pollution mapper of claim 1, wherein the pollution levels are based on a ratio of a number of relative changes in pollution with time that are above a predefined threshold over a period of time to the number of the plurality of pollution detectors that reported pollution information for each of the one or more locations and times over the period of time.

6. The traffic pollution mapper of claim 1, wherein the pollution information is transmitted to each of the plurality of client devices via one or more first wireless communication links, and the mapping information is received by the one or more servers via one or more second wireless communication links.

7. A traffic pollution mapper for one or more vehicles comprising:
a software application stored on a non-transitory storage medium that, when executed by one or more client devices, causes the one or more client devices to receive pollution information from one or more pollution detectors, and transmit the pollution information, location information generated by a location device, and one or more timestamps, the pollution information consisting of relative changes in pollution with time; and
one or more servers that receive and store the pollution information, location information and the one or more timestamps and generate one or more pollution maps that associate pollution levels with one or more locations and one or more times based on the relative changes in pollution with time, the location information, and the one or more timestamps;
wherein the one or more pollution detectors are installed on a subset of a plurality of vehicles and detect pollution variations and output pollution information based on the pollution variations;
wherein the one or more vehicles comprise one or more recirculation flaps that are closed or opened based on the one or more pollution maps to reduce exposure to pollution in the one or more vehicles, wherein at least one of the one or more vehicles is outside the subset and is not involved in detecting the pollution variations.

8. The traffic pollution mapper of claim 7, wherein the one or more servers provide access to the mapping information stored thereon upon receipt of a request for the mapping information by the one or more client devices.

9. The traffic pollution mapper of claim 7, wherein one or more routes that minimize pollution exposure for one or more occupants of the one or more vehicles are selected for traversal from the one or more pollution maps.

10. The traffic pollution mapper of claim 7, wherein the software application also causes each of the one or more client devices to present pollution information on a screen of each of the one or more client devices.

11. The traffic pollution mapper of claim 7, wherein the pollution information is wirelessly transmitted to the one or more client devices by the one or more pollution detectors.

12. The traffic pollution mapper of claim 7, wherein the mapping information is received by the one or more servers via a wireless communication link between the one or more servers and the one or more client devices.

13. The traffic pollution mapper of claim 7, wherein the one or more vehicles comprise one or more recirculation flaps that are closed or opened based on the one or more pollution maps to reduce exposure to pollution in the plurality of vehicles.

14. A method for generating and using a traffic pollution map to control one or more recirculation flaps at one or more vehicles comprising:
generating pollution information consisting of relative changes in pollution with time at a plurality of pollution detectors, wherein each pollution detector is installed at each vehicle in a subset of a plurality of vehicles;
generating location information and one or more timestamps;
receiving and storing the pollution information, the location information, and the one or more timestamps at one or more servers;
generating from the relative changes in pollution with time one or more pollution maps that associate pollution levels with one or more locations and one or more times based on the pollution information, the location information, and the one or more timestamps; and
transmitting the one or more pollution maps from the one or more servers to the one or more vehicles in response to the one or more requests;
wherein the one or more recirculation flaps are closed or opened based on the one or more pollution maps transmitted to the one or more vehicles by the one or more servers to reduce exposure to pollution in the one or more vehicles, wherein at least one of the one or more vehicles is outside the subset and is not involved in generating the pollution information.

15. The method of claim 14, wherein the pollution information comprises one or more binary recirculation flap open and close signals for purposes of generating the one or more pollution maps.

16. The method of claim 14, wherein one or more routes that minimize pollution exposure for one or more occupants of the one or more vehicles are selected for traversal from the one or more pollution maps.

17. The method of claim 14 further comprising providing a software application that is executable by one or more client devices, wherein when executed the software application causes the one or more client devices to receive the pollution information from the one or more pollution detectors and display the pollution information on a screen of the one or more client devices.

18. The method of claim 14, wherein the pollution information comprises pollution peak characteristics consisting of a relative increase in pollution level relative to time.

19. The method of claim 14, wherein the pollution levels are based on a ratio of a number of relative changes in pollution with time that are above a predefined threshold over a period of time to the number of the plurality of pollution detectors that reported pollution information for each of the one or more locations and times over the period of time.

* * * * *